United States Patent
Okada

(10) Patent No.: US 11,413,034 B2
(45) Date of Patent: Aug. 16, 2022

(54) METHOD FOR CLOSING WOUND

(71) Applicant: OLYMPUS CORPORATION, Hachioji (JP)

(72) Inventor: Tsutomu Okada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 120 days.

(21) Appl. No.: 17/069,150

(22) Filed: Oct. 13, 2020

(65) Prior Publication Data

US 2022/0110624 A1     Apr. 14, 2022

(51) Int. Cl.
| | | |
|---|---|---|
| A61B 17/04 | (2006.01) | |
| A61B 17/29 | (2006.01) | |
| A61B 17/06 | (2006.01) | |
| A61B 17/00 | (2006.01) | |

(52) U.S. Cl.
CPC ...... *A61B 17/0469* (2013.01); *A61B 17/0482* (2013.01); *A61B 17/29* (2013.01); *A61B 17/06066* (2013.01); *A61B 17/06166* (2013.01); *A61B 2017/0034* (2013.01)

(58) Field of Classification Search
CPC ........ A61B 2017/0034; A61B 17/0469; A61B 17/0482; A61B 17/29; A61B 17/06066; A61B 17/06166; D05B 91/00; D05B 91/02

See application file for complete search history.

(56) References Cited

U.S. PATENT DOCUMENTS

| | | | | |
|---|---|---|---|---|
| 5,129,912 A | * | 7/1992 | Noda | A61B 17/0469 606/147 |
| 5,234,445 A | * | 8/1993 | Walker | A61B 17/12013 606/139 |
| 5,250,054 A | * | 10/1993 | Li | A61B 17/0469 606/1 |
| 5,423,836 A | * | 6/1995 | Brown | A61B 17/0469 606/139 |
| 5,702,407 A | * | 12/1997 | Kaji | A61B 17/0469 606/139 |
| 5,709,694 A | * | 1/1998 | Greenberg | A61B 17/0483 606/147 |
| 5,954,731 A | * | 9/1999 | Yoon | A61B 17/062 606/147 |
| 5,954,733 A | * | 9/1999 | Yoon | A61B 18/1445 606/147 |
| 5,957,937 A | * | 9/1999 | Yoon | A61B 18/1445 606/147 |
| 5,984,932 A | * | 11/1999 | Yoon | A61B 17/0469 606/147 |

(Continued)

*Primary Examiner* — Phong Son H Dang
(74) *Attorney, Agent, or Firm* — Oliff PLC

(57) ABSTRACT

A method for closing a wound in a tubular organ using a suture thread attached to a suture needle. The method includes grasping a first part of the suture thread by a grasper inserted in the tubular organ after the suture thread has been passed through tissue surrounding the wound at a first position; moving the first part away from the first position by moving the grasper grasping the first part along a longitudinal axis of the grasper; grasping a second part of the suture thread located between the first part and the first position by the grasper; and moving the second part away from the first position by moving the grasper grasping the second part along the longitudinal axis of the grasper.

10 Claims, 23 Drawing Sheets

(56) References Cited

U.S. PATENT DOCUMENTS

| | | | | |
|---|---|---|---|---|
| 5,993,466 A * | 11/1999 | Yoon | ................. | A61B 18/1445 |
| | | | | 606/147 |
| 6,004,332 A * | 12/1999 | Yoon | ................. | A61B 17/0469 |
| | | | | 606/139 |
| 6,086,601 A * | 7/2000 | Yoon | .................... | A61B 17/062 |
| | | | | 606/147 |
| 6,099,553 A * | 8/2000 | Hart | ................... | A61B 17/0487 |
| | | | | 606/232 |
| 9,888,915 B2 * | 2/2018 | Torrie | ................ | A61B 17/0485 |
| 2005/0171561 A1 * | 8/2005 | Songer | ............... | A61B 17/0469 |
| | | | | 606/144 |
| 2013/0310853 A1 * | 11/2013 | Zaugg | ................ | A61B 17/0401 |
| | | | | 606/232 |
| 2015/0142021 A1 | 5/2015 | Smith et al. | | |
| 2021/0275167 A1 * | 9/2021 | Bedoya | .............. | A61B 17/0483 |
| 2021/0361281 A1 * | 11/2021 | O'Shea | ................. | A61B 34/71 |

* cited by examiner

METHOD FOR CLOSING WOUND

BACKGROUND

Technical Field

The present invention relates to a method for closing a wound, more specifically, a method for closing a wound formed in a tubular organ under observation with a flexible endoscope.

Background Art

Endoscopic submucosal dissection (ESD) is becoming widespread as one of the treatments for gastrointestinal tumors. After the ESD procedure, a wider range of mucosal defects occur than in endoscopic mucosal resection (EMR). From the viewpoint of promoting recovery, it is preferable to close the defective site.

Clips are known as a means for transendoscopically closing wounds such as mucosal defects, but since mucosal defects due to ESD are large, it is often impossible to close them with clips.

Another means of closing a wound is suturing with a suture thread. By tracting the suture thread around the wound, the periphery of the wound approaches and the wound is closed.

Devices for transendoscopic suturing have been proposed.

The device described in United States patent application, Publication No. 2015/0142021 sutures tissue by tracting a thread held by a snare or hook and attaching the thread fastener to prevent loosening of the thread through the tissue.

SUMMARY

The present invention is a method for closing a wound in a tubular organ using a suture thread attached with a suture needle. The method has the following steps: a step of grasping a first part of the suture thread by a grasper inserted in the tubular organ, the suture thread having passed through a first position of a surrounding tissue of the wound; a step of moving the first part away from the first position by moving the grasper grasping the first part along a longitudinal axis of the grasper; a step of grasping a second part of the suture thread by the grasper, the second part being located between the first part and the first position; and a step of moving the second part away from the first position by moving the grasper grasping the second part along the longitudinal axis of the grasper.

Another aspect of the present invention has the following steps: a step of grasping a first part of the suture thread by a first grasper inserted in the tubular organ, the suture thread having passed through a first position of a surrounding tissue of the wound; a step of moving the first part away from the first position by moving the first grasper grasping the first part along a longitudinal axis of the first grasper; a step of grasping a second part of the suture thread by a second grasper inserted in the tubular organ, the second part being located between the first part and the first position; and a step of moving the second part away from the first position by moving the second grasper grasping the second part along a longitudinal axis of the second grasper.

DETAILED DESCRIPTION OF THE PREFERRED EMBODIMENTS

A first embodiment of the present invention will be described with reference to FIGS. 1 to 7.

As a preparatory work, a flexible endoscope having a flexible insertion part is inserted into a tubular organ through a target's mouth or nose, and the distal end of the flexible endoscope is moved to a vicinity of a wound to be closed.

Next, a first grasper capable of grasping a suture thread and a second grasper different from the first grasper are introduced in the vicinity of the wound. The first grasper and the second grasper are, for example, an elongated forceps or a needle holder used together with a flexible endoscope, and either double-opening or single-opening can be used. The first grasper and the second grasper can be introduced into the body by passing through a channel of the endoscope, passing through an external channel attached to the endoscope, bundling with a band or the like in the endoscope, and the like.

In a case where the wound is a mucosal defect after the ESD procedure, the operator may temporarily remove the flexible endoscope from the tubular organ after the ESD procedure, protrude the distal end of the first grasper from the distal end opening of the channel of the flexible endoscope, and, with a suture needle or a suture thread attached to the suture needle grasped by the distal end of the first grasper, reinsert the first grasper with the flexible endoscope into the tubular organ.

When the suture thread is tracted through the suture thread in the two tissues facing each other across the wound, the two tissues approach each other. The wound can be closed by forming a plurality of pairs of two tissues according to the number of wounds.

When closing a large wound, it is necessary to pass a suture thread through many parts of the tissue around the wound (hereinafter, referred to as "surrounding tissue"). In addition, the amount of traction required to pass the suture thread through the many parts is also increased.

The present invention has a major feature in the traction mode of the suture thread. In the following, a suture thread traction operation according to the present embodiment will be further described with reference to an example in which the first grasper and the second grasper are passed through the channel of the endoscope.

Figure 1:
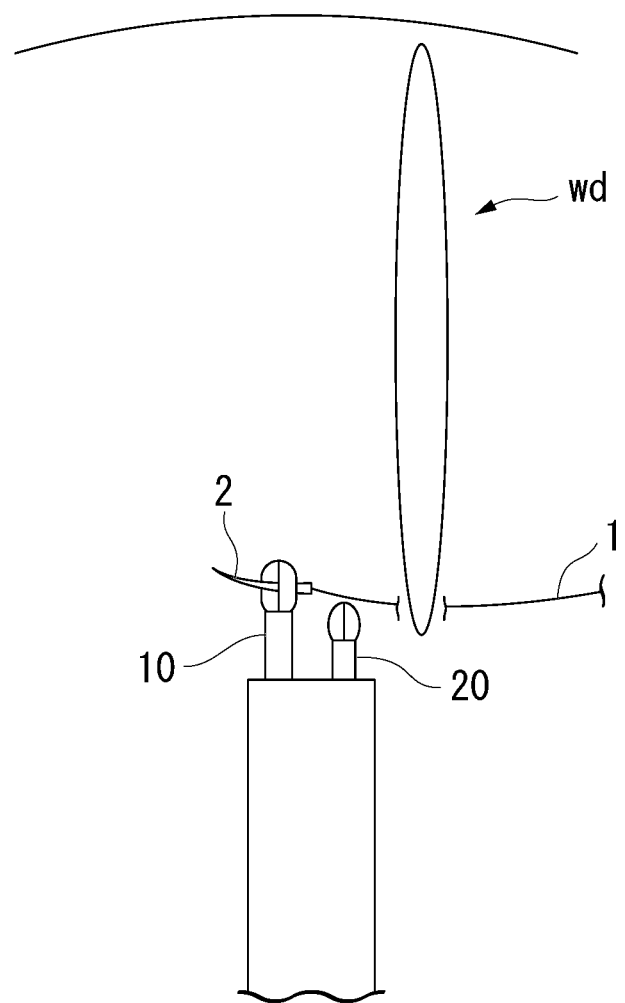
FIG. 1 is a view showing step A of a method for closing a wound according to a first embodiment of the present invention.

FIG. 1 shows a suture thread 1 threaded through the wound wd. The suture thread 1 can be arranged so as to intersect the wound wd by passing a curved needle 2 attached to the suture thread through two points of the surrounding tissue of the wound wd. In order to close the wound wd by continuous suturing with the suture thread 1, it is necessary to further pass the curved needle 2 through the surrounding tissue, and therefore it is necessary to tract the suture thread 1.

The operator brings the first grasper 10 and the second grasper 20 closer to the suture thread 1, and as shown in FIG. 1, grasps the suture thread 1 with the first grasper 10, which has a distance from the wound wd larger than that of the second grasper 20 (step A). When performing step A, the first grasper 10 may grasp the curved needle 2 attached to the suture thread 1 as shown in FIG. 1 or may grasp the suture thread 1 itself.

Figure 2:
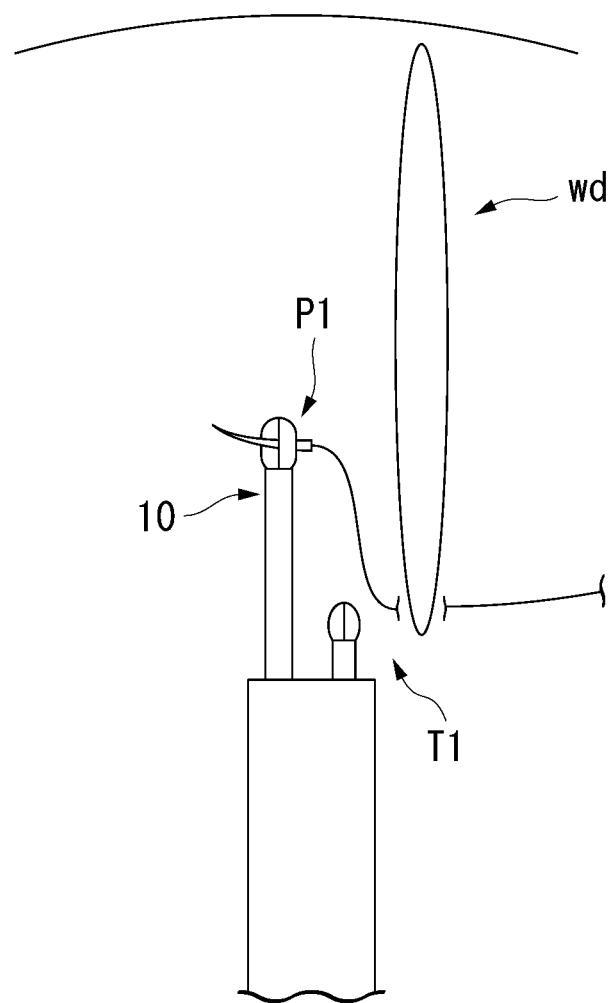
FIG. 2 is a view showing step B of the method for closing.

Next, as shown in FIG. 2, the operator advances the first grasper 10 grasping the suture thread 1 so as to move the grasped part (first part) P1 of the suture thread 1 grasped by the first grasper 10 away from the position (first position) T1 of the surrounding tissue through which the suture thread was immediately passed (step B).

By step B, the suture thread 1 is tracted by an increase in the distance between the grasped part P1 grasped by the first grasper 10 and the position T1.

Figure 3:
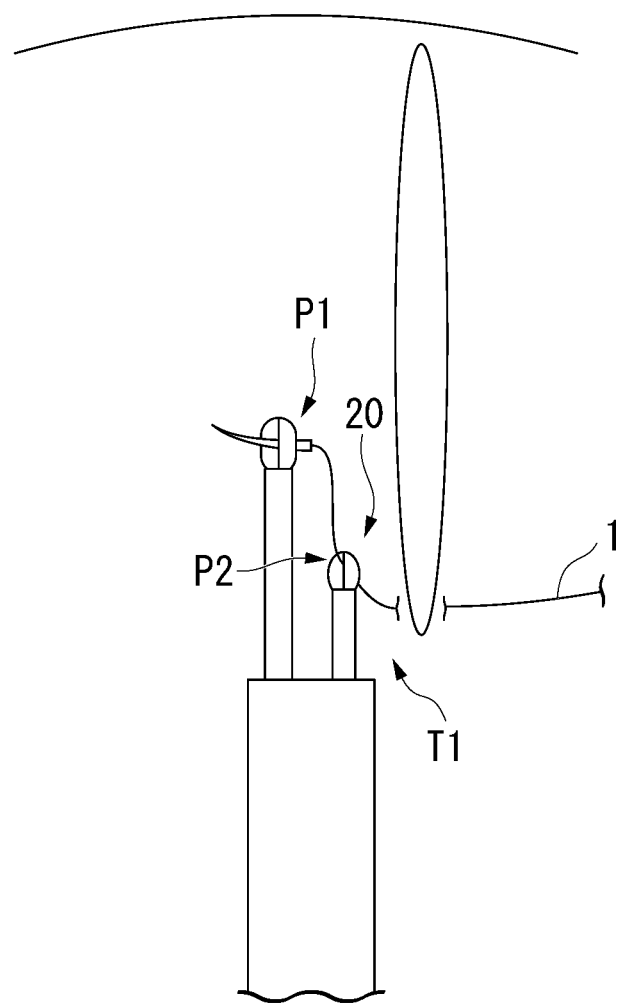
FIG. 3 is a view showing step C of the method for closing.
Figure 4:
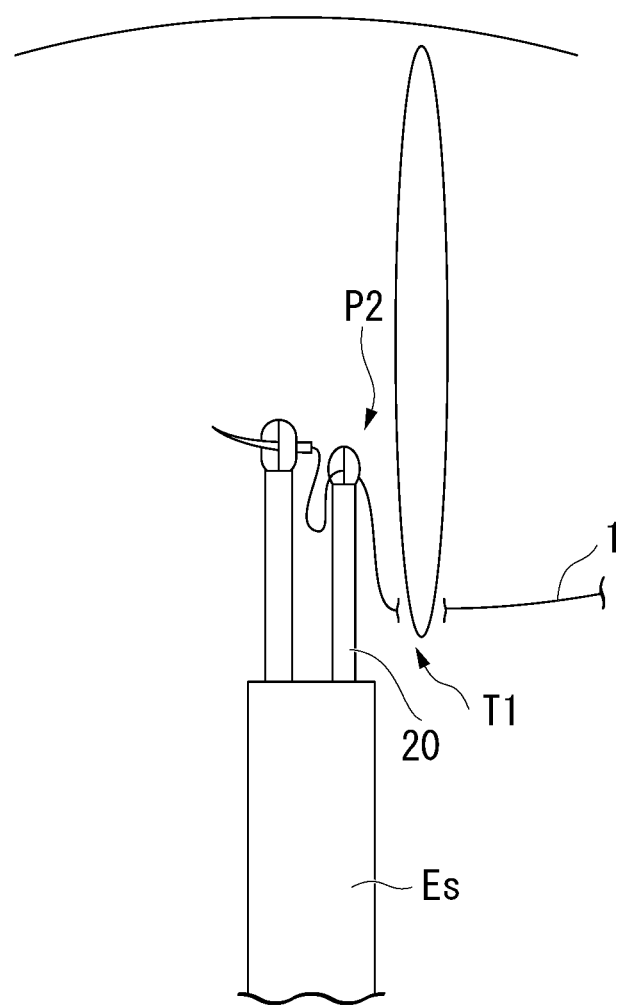
FIG. 4 is a view showing step D of the method for closing.

Next, as shown in FIG. 3, the operator grasps the grasped part (second part) P2 of the suture thread 1 extending between the grasped part P1 and the position T1 by the second grasper 20 (step C). Further, as shown in FIG. 4, the operator advances the second grasper 20 grasping the suture thread 1 in the longitudinal axis direction so as to move the grasped part P2 grasped by the second grasper 20 away from the position T1 (step D).

By step D, the suture thread 1 is tracted by an increase in the distance between the grasped part P2 and the position T1. Therefore, in step C, it is preferable to grasp the position close to the position T1 with the second grasper, and the endoscope Es may be operated if necessary.

Figure 5:
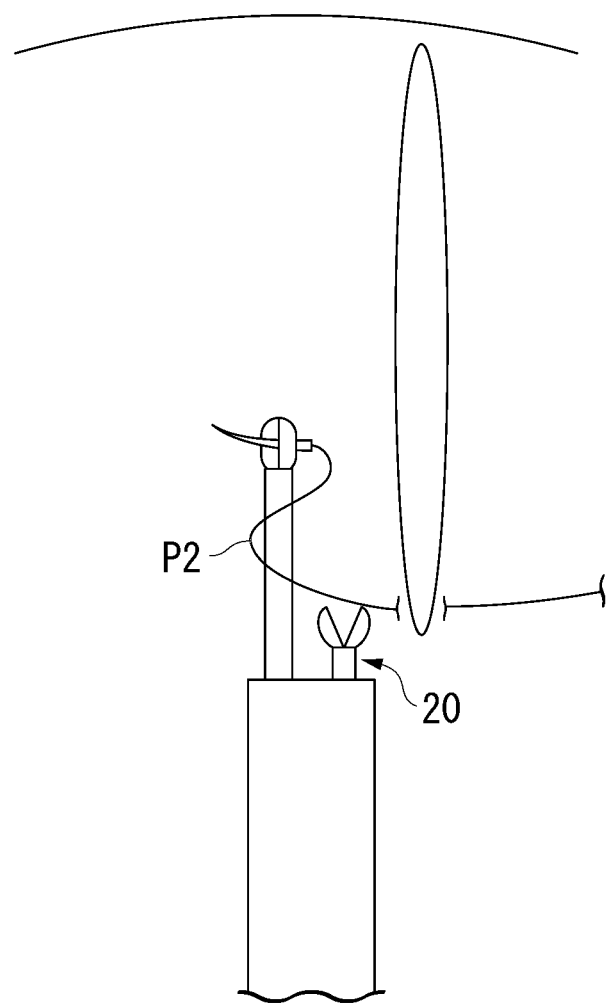
FIG. 5 is a view showing step E of the method for closing.
Figure 6:
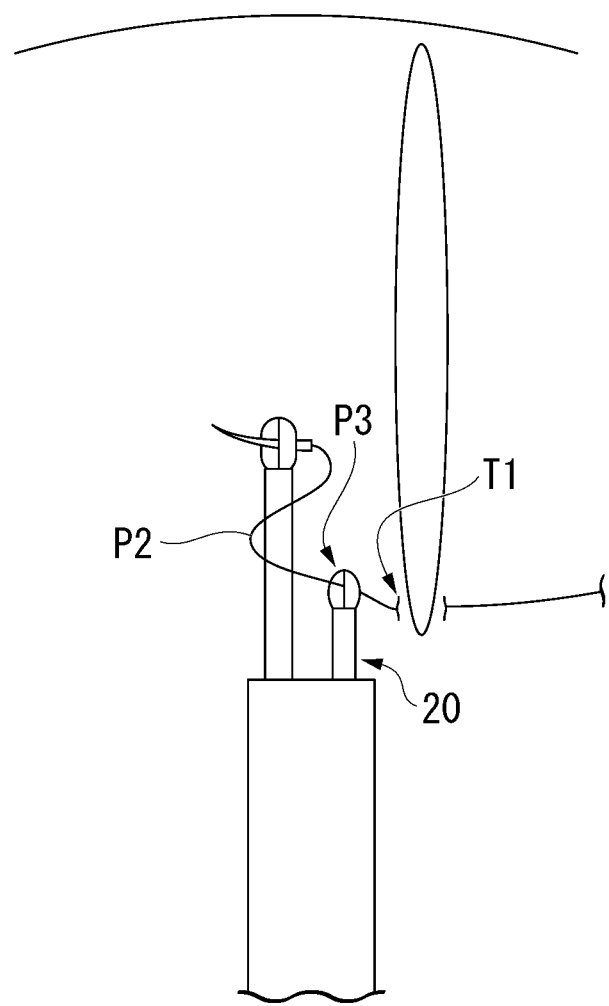
FIG. 6 is a view showing step C1 of the method for closing.

As shown in FIG. 5, the operator releases the grasping of the grasped part P2 by the second grasper 20 and retracts the second grasper 20 in the longitudinal axis direction (step E). Further, as shown in FIG. 6, the operator grasps the grasped part P3 of the suture thread 1 by the second grasper 20 (step C1). The operation itself of step C1 is substantially the same as that of step C, and it can be said that it is one aspect of step C. However, in step C1, the grasped part P3 located between the grasped part P2 and the position T1 is grasped by the second grasper 20.

In step C1, the suture thread 1 may be adjusted to a position where it can be easily grasped by the second grasper 20 by rotating the endoscope Es or the first grasper 10 around the longitudinal axis, if necessary.

The operator then iterates the setting of steps C to E until the suture thread 1 is tracted from the position T1 to a desired length and temporarily ends the suture thread traction operation. The final set of iterations does not necessarily have to go to step E and may end at step D.

After the traction operation is completed, the suture thread 1 is passed by penetrating the curved needle 2 through the surrounding tissue, and the suture thread traction operation is performed again. After passing the suture thread 1 through the surrounding tissue a sufficient number of times to close the wound wd, the wound wd is sewn and closed.

Figure 7:
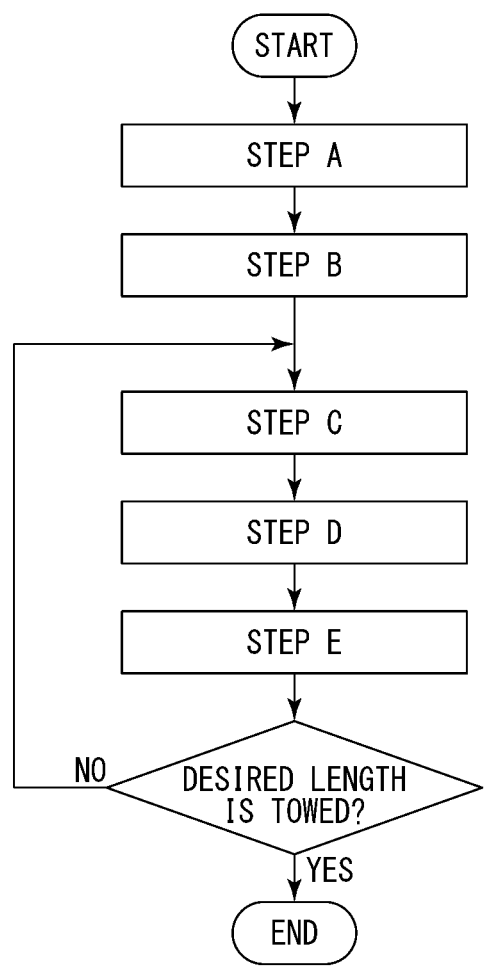
FIG. 7 is a flowchart showing a flow of a suture thread traction operation according to the first embodiment.

The flow of the suture thread traction operation in the first embodiment is shown in FIG. 7 in a flowchart.

As described above, according to the method for closing a wound according to the present embodiment, the suture thread 1 can be tracted only by combining the operation of grasping the suture thread 1 by the first grasper 10 with the steps B, D, and E of repeatedly advancing and retreating the second grasper 20. As a result, a needle holder or the like having a simple structure that does not have an active bending function can be used as the first grasper and the second grasper.

In addition, since the wound can be closed as long as a space is secured for the second grasper to advance and retreat, the method can be smoothly performed even in a narrow tubular organ.

A second embodiment of the present invention will be described with reference to FIGS. 8 to 12. In the following description, with respect to the steps and configurations already described, the same reference numerals are given, and duplicate description will be omitted as appropriate.

First, steps A to D are performed in the same procedure as in the first embodiment.

Figure 8:
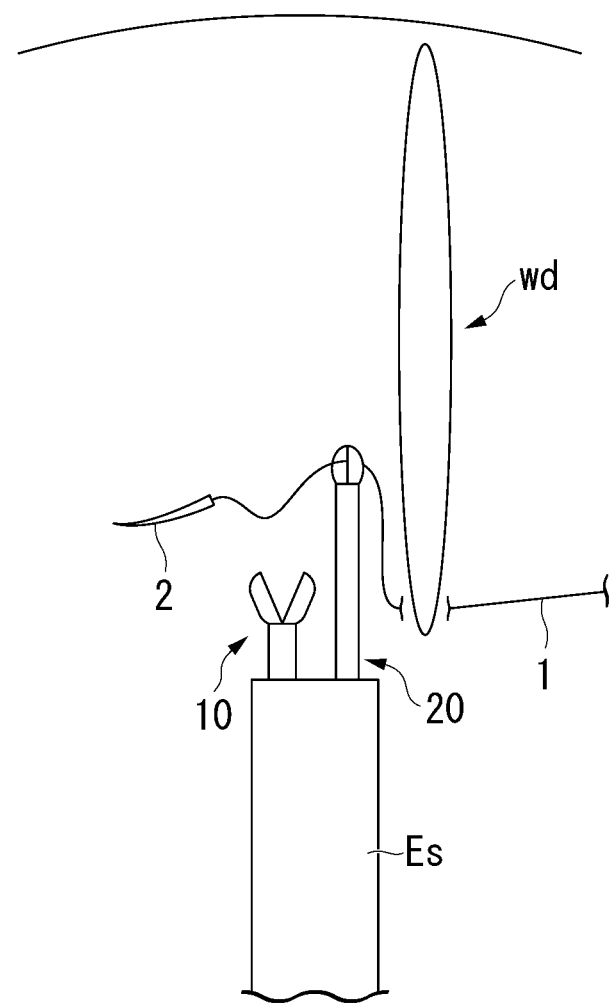
FIG. 8 is a view showing step F of a method for closing a wound according to a second embodiment of the present invention.

Following step D, as shown in FIG. 8, the grasping of the suture thread 1 by the first grasper 10 is released and the first grasper 10 is retracted (step F).

Figure 9:
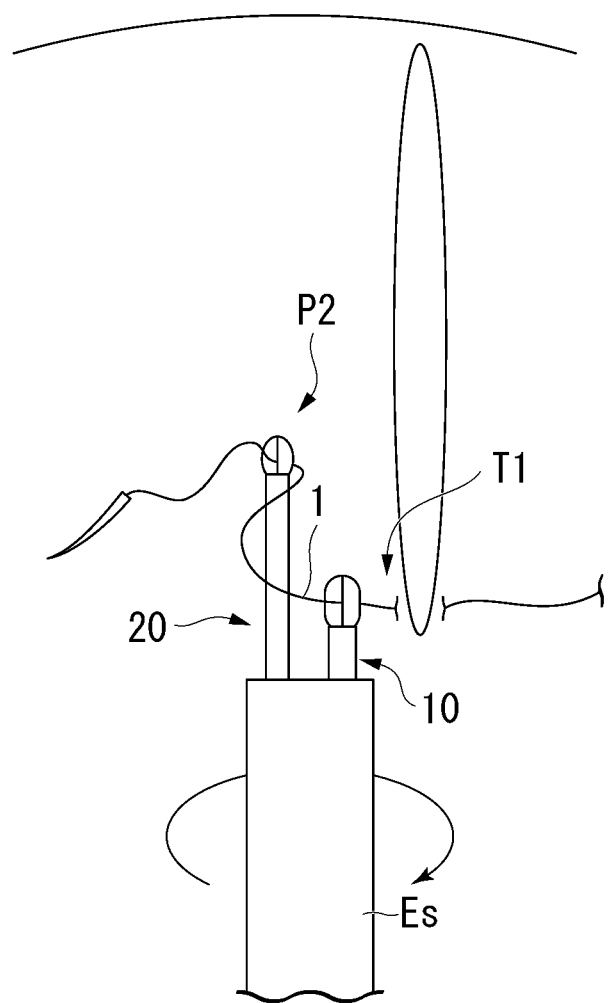
FIG. 9 is a view showing step G of the method for closing.

Next, the suture thread 1 is grasped by the first grasper 10 at a position between the grasped part P2 and the position T1 (step G). In order to bring the first grasper 10 closer to the suture thread 1 between the grasped part P2 and the position T1, it is a convenient method to rotate the endoscope Es around the longitudinal axis as shown in FIG. 9. Alternatively, the first grasper 10 may be brought closer to the suture thread 1 by bending the endoscope Es or advancing and retreating the endoscope Es.

Figure 10:
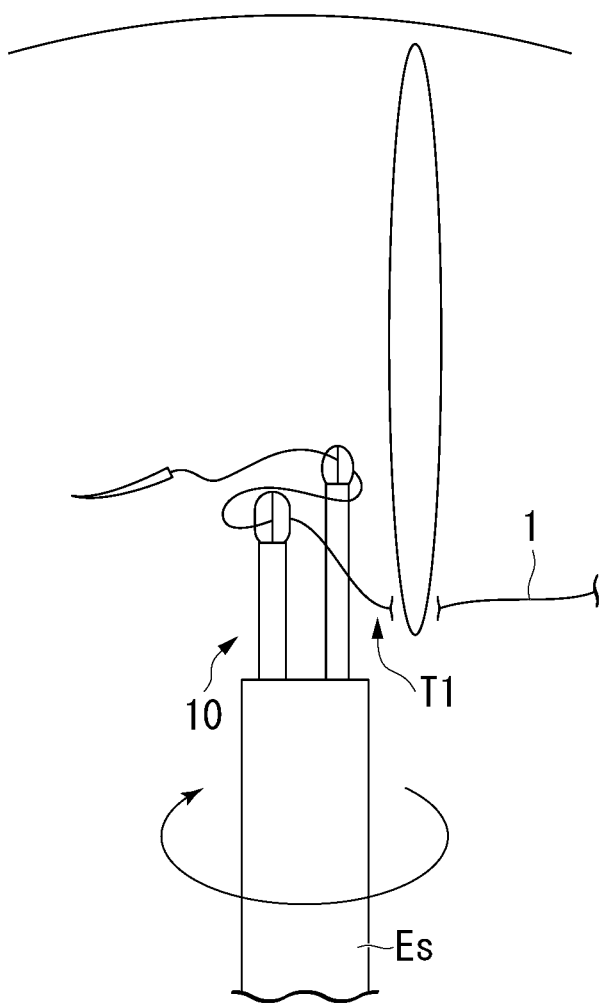
FIG. 10 is a view showing step H of the method for closing.

Next, as shown in FIG. 10, the first grasper 10 grasping the suture thread 1 is moved away from the position T1 (step H). Since FIG. 10 is a view following FIG. 9, it is a view showing that the endoscope Es is rotated in the direction opposite to step G. However, in step H, the specific operation of moving the first grasper 10 away from the position T1 can be appropriately set.

The first grasper 10 may be advanced or retracted in step H.

Figure 11:
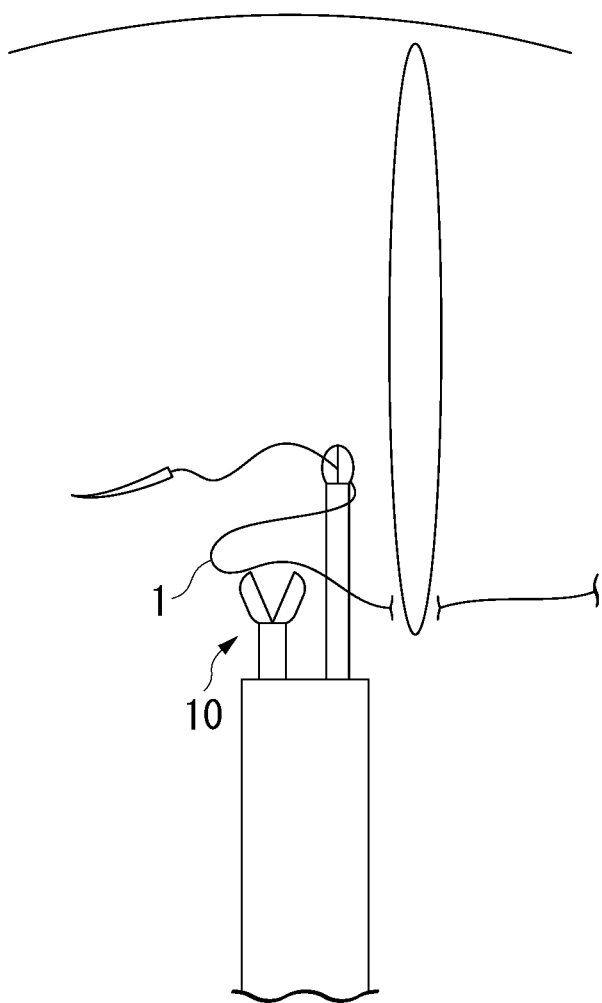
FIG. 11 is a view showing step I of the method for closing.

Next, as shown in FIG. 11, the grasping of the suture thread 1 by the first grasper 10 is released (step I).

The operator then iterates the set of steps G to I until the suture thread 1 is tracted from the position T1 to a desired length, and temporarily ends the suture thread traction operation. The final set of iterations does not necessarily have to go to step I and may end at step H.

Figure 12:
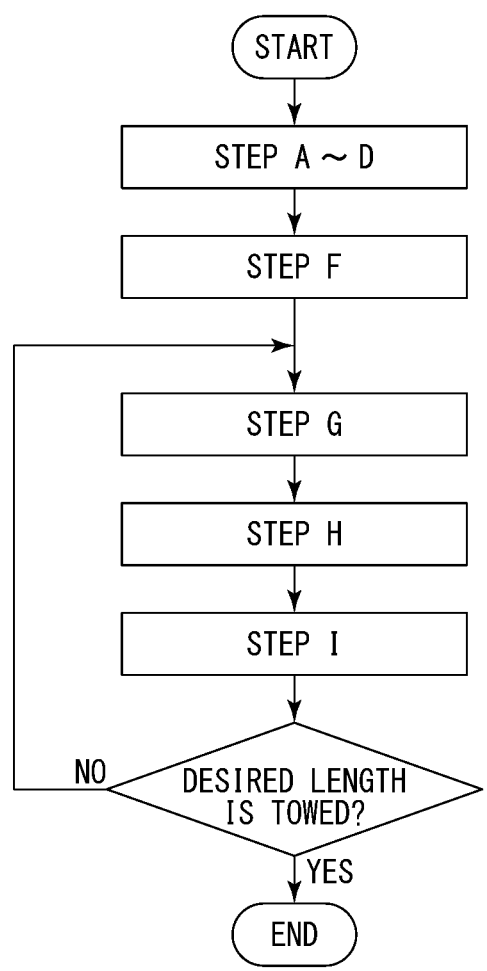
FIG. 12 is a flowchart showing a flow of a suture thread traction operation according to the second embodiment.

The flow of the suture thread traction operation in the second embodiment is shown in FIG. 12 in a flowchart.

According to the method for closing a wound according to the present embodiment, the suture thread 1 can be tracted only by combining the operation of grasping the suture thread by the first grasper 10 or the second grasper 20 with the step of advancing and retreating the first grasper 10 or the second grasper 20. As a result, the same effect as that of the first embodiment is obtained.

A third embodiment of the present invention will be described with reference to FIGS. 13 to 15.

First, steps A to I are performed in the same procedure as in the second embodiment.

Figure 13:
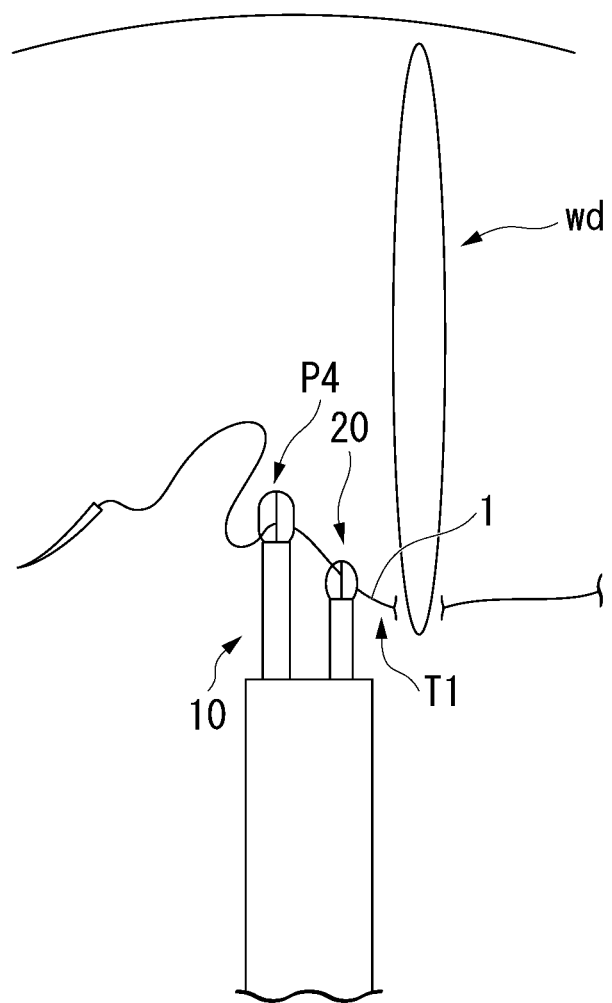
FIG. 13 is a view showing step J of a method for closing a wound according to a third embodiment of the present invention.

Following step I, as shown in FIG. 13, the suture thread 1 is grasped by the second grasper 20 at a position between the grasped part P4 and the position T1 where the first grasper 10 grasps the suture thread 1. (Step J).

Figure 14:
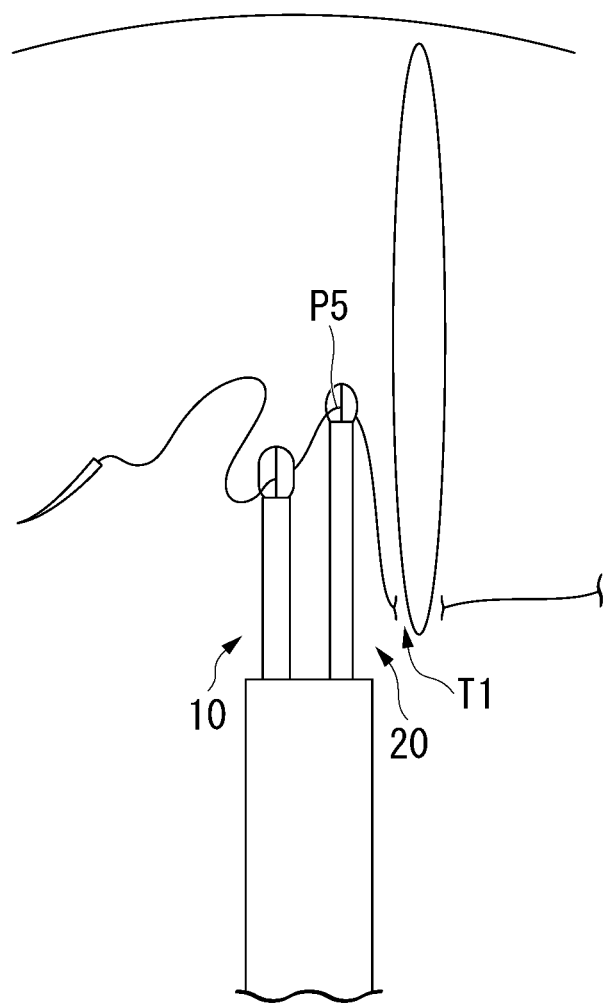
FIG. 14 is a view showing step K of the method for closing.

Subsequently, as shown in FIG. 14, by advancing the second grasper 20 grasping the suture thread 1, the grasped part P5 grasped by the second grasper 20 is moved away from the position T1 (step K). In FIG. 14, although the first grasper 10 is advancing together with the second grasper 20, the movement of the first grasper 10 in step K can be changed. For example, the position of the first grasper 10 may not be changed by releasing the grasping of the suture thread 1 by the first grasper 10.

Figure 15:
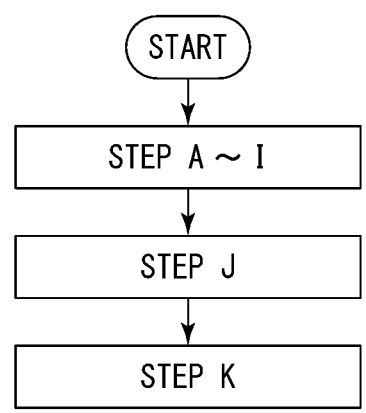
FIG. 15 is a flowchart showing part of the flow of a suture thread traction operation according to the third embodiment.

The above flow is shown in FIG. 15 in a flowchart.

After performing step K, the set of steps C, D, and E, or the set of steps J and K is performed until the suture thread 1 is tracted from the position T1 to the desired length, and the suture thread traction operation is temporarily ended. The set of steps C, D and E and the set of steps J and K can be freely combined, and only one of them may be performed.

The method for closing a wound according to the present embodiment simply combines the operation of grasping the suture thread with the first grasper 10 or the second grasper 20 with the step of advancing and retreating the first grasper 10 or the second grasper 20, so that the suture thread 1 can be tracted. As a result, the same effects as those of the first embodiment and the second embodiment are obtained.

The first to third embodiments are suitable in a case where the position of the tissue through which the suture thread has been passed immediately before is relatively close to the endoscope Es as in position T1.

A fourth embodiment of the present invention will be described with reference to FIGS. 16 to 22.

Figure 16:
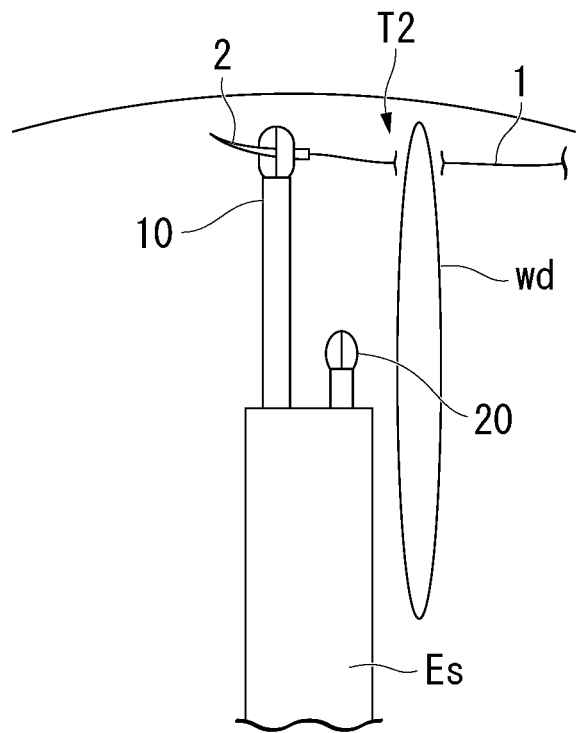
FIG. 16 is a view showing step L of a method for closing a wound according to a fourth embodiment of the present invention.

As shown in FIG. 16, the operator grasps the suture thread 1 with the first grasper 10 having a large distance from the wound wd (step L). The operation of step L is similar to step A in the first embodiment, but is different in that the position T2 of the tissue through which the suture thread 1 was passed immediately before is separated from the distal end of the endoscope Es than the position T1 in the first embodiment.

Figure 17:
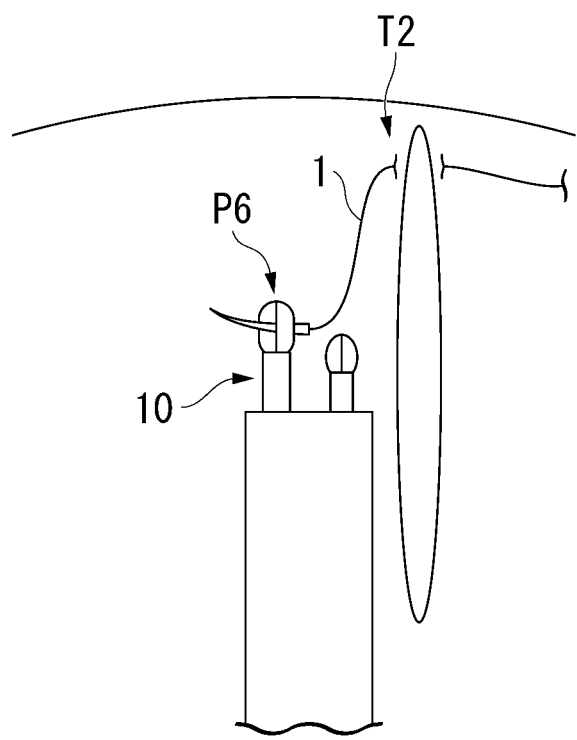
FIG. 17 is a view showing step M of the method for closing.

Subsequently, as shown in FIG. 17, the operator retracts the first grasper 10 to move the grasped part P6 grasped by the first grasper 10 away from the position T2 (step M). By step M, the suture thread 1 is tracted by an increase in the distance between the grasped part P6 and the position T2.

Figure 18:
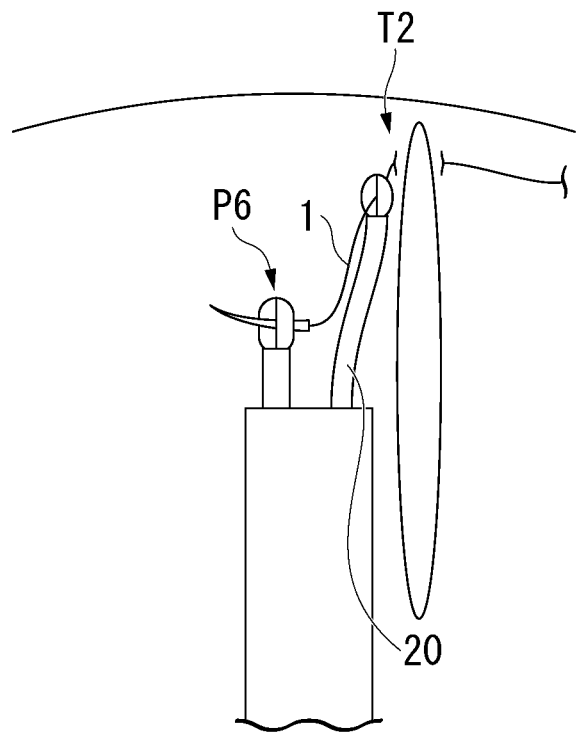
FIG. 18 is a view showing step N of the method for closing.
Figure 19:
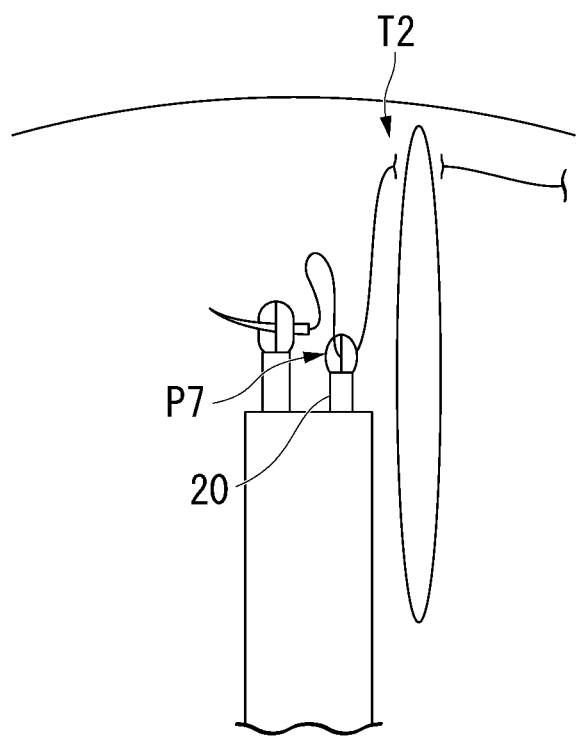
FIG. 19 is a view showing step O of the method for closing.

Subsequently, as shown in FIG. 18, in a state where the second grasper 20 is advanced, the operator grasps the suture thread 1 by the second grasper 20 at a position between the grasped part P6 and the position T2 (Step N). Further, the operator retracts the second grasper 20 while grasping the suture thread 1, and moves the grasped part P7 grasped by the second grasper 20 away from the position T2 as shown in FIG. 19 (step O). By step O, the suture thread 1 is tracted by an increase in the distance between the grasped part P7 and the position T2.

Figure 20:
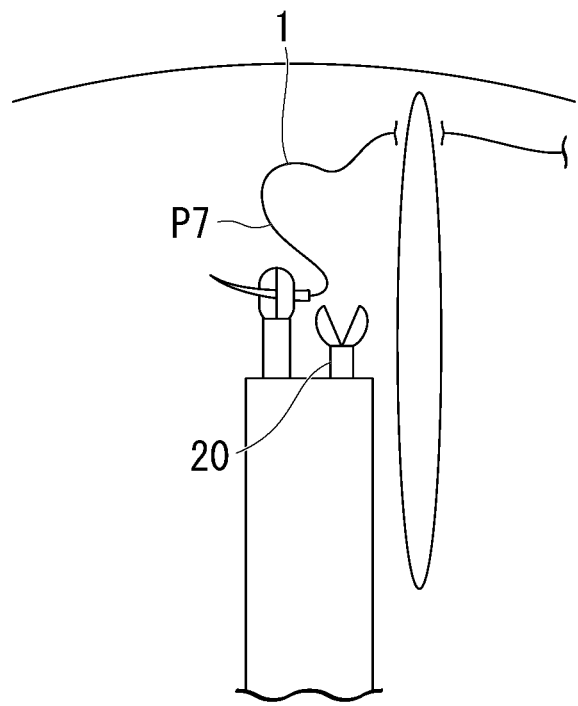
FIG. 20 is a view showing step P of the method for closing.
Figure 21:
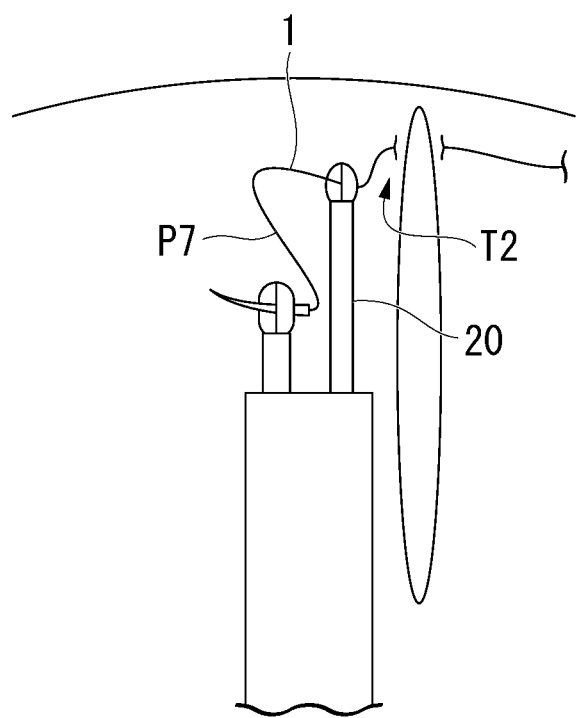
FIG. 21 is a view showing step N1 of the method for closing.

Subsequently, as shown in FIG. 20, the operator releases the grasping of the grasped part P7 by the second grasper 20 (step P), and as shown in FIG. 21, grasps the suture thread 1 by the second grasper 20 at a position between the grasped part P7 and the position T2 (step N1). The operation itself of step N1 is substantially the same as that of step N and can be said to be one aspect of step N.

The operator then iterates the set of steps N to P until the suture thread 1 is tracted from the position T2 to a desired length and temporarily ends the suture thread traction operation. The final set of iterations does not necessarily have to go to step P and may end at step O.

Figure 22:
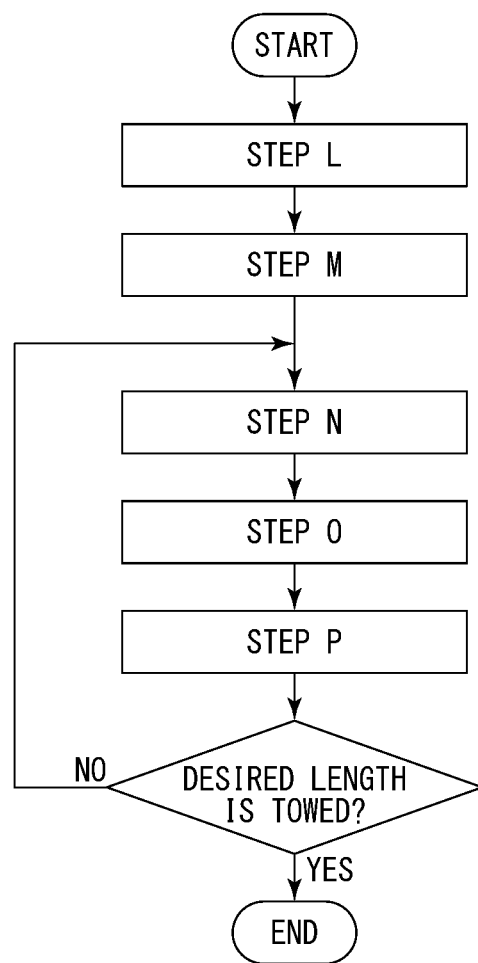
FIG. 22 is a flowchart showing a flow of a suture thread traction operation according to the fourth embodiment.

The flow of the suture thread traction operation in the fourth embodiment is shown in FIG. 22 in a flowchart.

The method for closing a wound according to the present embodiment tracts the suture thread 1 only by combining the operation of grasping the suture thread by the first grasper 10 with the step of advancing and retreating the first grasper 10 or the second grasper 20. As a result, the same effects as those of the first to third embodiments are obtained.

A fifth embodiment of the present invention will be described with reference to FIGS. 23 to 26.

First, steps L to O are performed in the same procedure as in the fourth embodiment.

Figure 23:
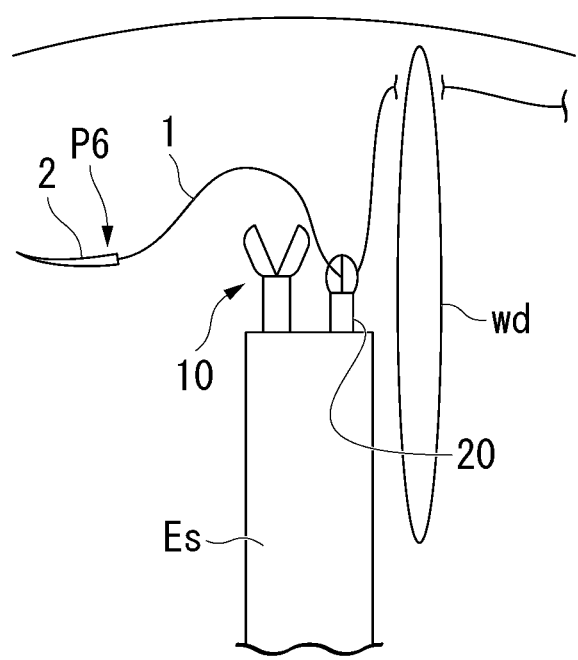
FIG. 23 is a view showing step Q of a method for closing a wound according to a fifth embodiment of the present invention.
Figure 24:
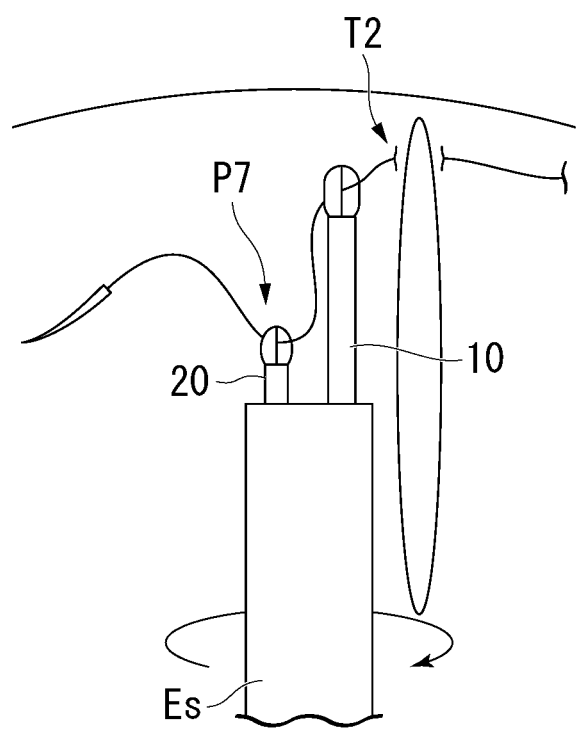
FIG. 24 is a view showing step R of the method for closing.

Following step O, the operator releases the grasping of the grasped part P6 by the first grasper 10 as shown in FIG. 23 (step Q), and grasps the suture thread 1 by the first grasper 10 at a position between the grasped part P7 grasped by the second grasper 20 and the position T2 as shown in FIG. 24 (step R).

In step R, it is preferable to grasp the suture thread 1 with the first grasper 10 at a position close to the position T2. Therefore, similarly to step H described above, the endoscope Es may be operated to bring the first grasper 10 closer to the position T2. FIG. 24 shows an example of rotating the endoscope Es around the longitudinal axis.

Figure 25:
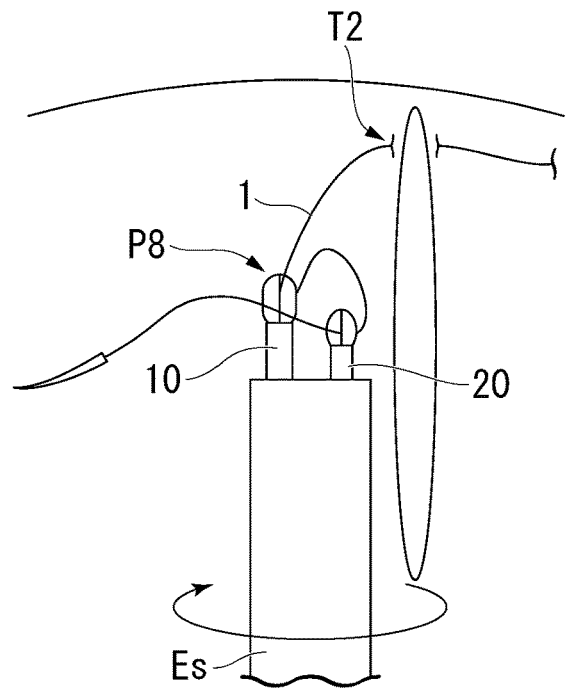
FIG. 25 is a view showing step S of the method for closing.

Subsequently, the operator retracts the first grasper 20 while grasping the suture thread 1 to move the grasped part P8 away from the position T2 as shown in FIG. 25 (step S). By step S, the suture thread 1 is tracted by an increase in the distance between the grasped part P7 grasped by the first grasper 10 and the position T2.

Step S may be combined with the rotation operation of the endoscope Es. In the example shown in FIG. 25, the first grasper 20 is retracted while the endoscope Es is rotated around the longitudinal axis.

After that, the operator iterates the setting of steps Q to S until the suture thread 1 is tracted from the position T2 to a desired length and temporarily ends the suture thread traction operation.

Figure 26:
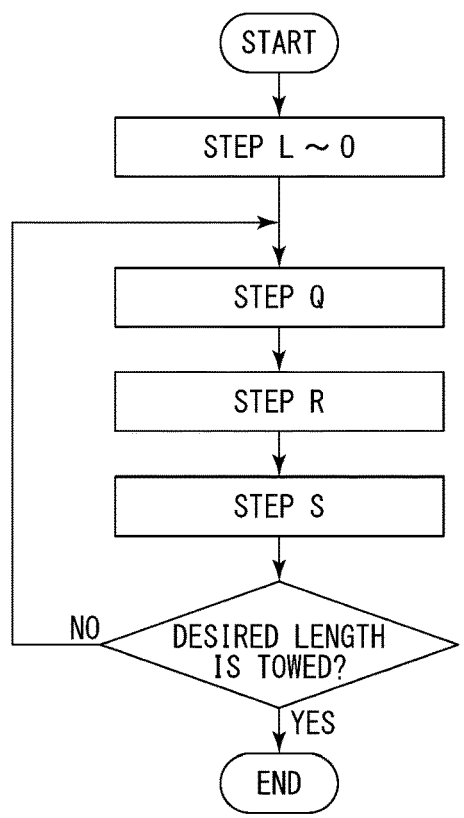
FIG. 26 is a flowchart showing a flow of a suture thread traction operation according to the fifth embodiment.

The flow of the suture thread traction operation in the fourth embodiment is shown in FIG. 26 in a flowchart.

The method for closing a wound according to the present embodiment simply combines the operation of grasping the suture thread by the first grasper 10 or the second grasper 20 with the step of advancing and retreating the first grasper 10 or the second grasper 20, so that the suture thread 1 can be tracted. As a result, the same effects as those of the first to fourth embodiments are obtained.

A sixth embodiment of the present invention will be described with reference to FIGS. 27 to 29.

First, steps L to O are performed in the same procedure as in the fourth embodiment.

Subsequently, steps Q to S are performed in the same procedure as in the fifth embodiment.

Figure 27:
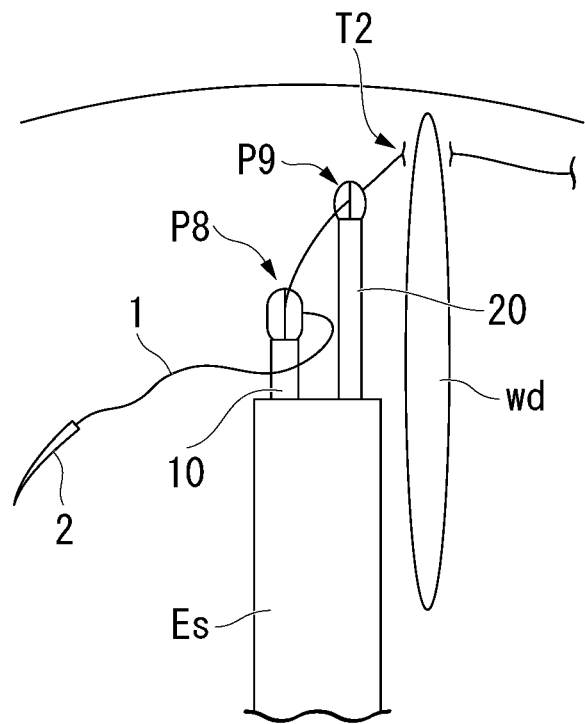
FIG. 27 is a view showing step T of a method for closing a wound according to a sixth embodiment of the present invention.
Figure 28:
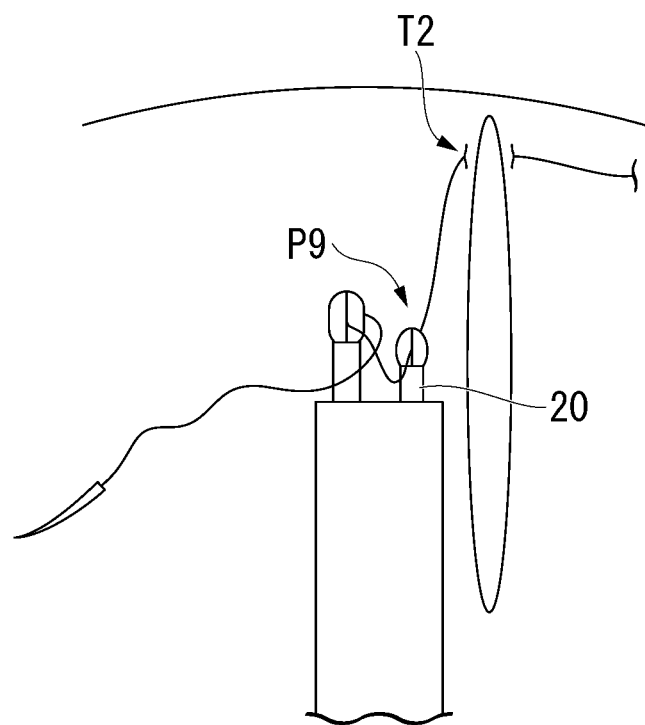
FIG. 28 is a view showing step U of the method for closing.

Subsequently, the grasping of the suture thread 1 by the second grasper 20 is released, and as shown in FIG. 27, in a state where the second grasper 20 is advanced, the suture thread 1 is grasped at the grasped part P9 located between the grasped part P8 and the position T2 (step T). Further, the second grasper 20 is retracted while grasping the grasped part P9, and the grasped part P9 is moved away from the position T2 as shown in FIG. 28 (step U).

Figure 29:
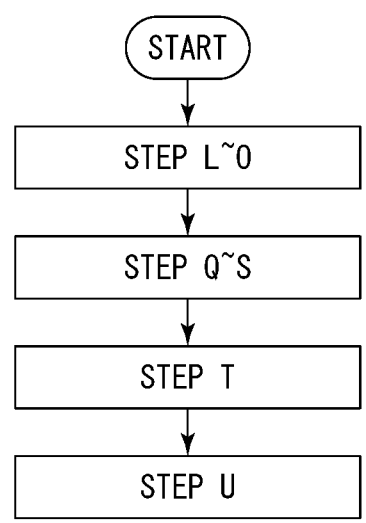
FIG. 29 is a flowchart showing part of the flow of a suture thread traction operation according to the sixth embodiment.

The above flow is shown in a flowchart in FIG. 29.

After performing step U, the set of steps Q, R, S, or the set of steps T and U is performed until the suture thread 1 is tracted from the position T2 to the desired length, and the suture thread traction operation is temporarily ended.

The set of steps Q, R, S and the set of steps T, U can be freely combined, and only one of them may be performed.

The method for closing a wound according to the present embodiment simply combines the operation of grasping the suture thread by the first grasper 10 or the second grasper 20 with the step of advancing and retreating the first grasper 10 or the second grasper 20, so that the suture thread 1 can be tracted. As a result, the same effects as those of the first to fifth embodiments are obtained.

The fourth to sixth embodiments are suitable in a case where the position of the tissue through which the suture thread has been passed immediately before is relatively far from the endoscope Es as in position T2.

While preferred embodiments of the present invention have been described and shown above, it should be understood that these are exemplary of the present invention and are not to be considered as limiting. Additions, omissions, substitutions, and other modifications can be made without departing from the spirit or scope of the present invention.

Some changes are shown below, but they are not all and other changes are possible. Two or more of these changes may be combined as appropriate, or may be combined with the above-mentioned changes.

The suture thread used in the present invention is not particularly limited, and each known main suture thread can be used. The use of a suture thread with an anti-loosening barb prevents the tracted suture thread from loosening before the celebration, making it easier to close the wound.

In the first and fourth embodiments, it is not necessary to keep the suture thread grasped by the first grasper. For example, after step B or step M, the suture thread may be temporarily grasped in the tubular organ by hooking the curved needle on the wall of the tubular organ.

In a series of operations such as iterating the set of steps C to E to repeatedly advance and retreat the same grasper, when releasing the grasping of the suture thread by the grasper, the suture thread is not necessarily completely separated from the grasper. For example, the grasped part may be changed while moving the grasper along the longitudinal axis of the suture, by sliding the grasper against the suture thread, in a state where the grasper is weakly sandwiched by the suture thread so that the grasper can slide with respect to the suture thread.

The operations described in each embodiment may be combined as appropriate when tracting the suture thread. For example, after performing one set of operations of the first embodiment, two sets of operations of the second embodiment may be performed.

What is claimed is:

1. A method for closing a wound in a tubular organ using a suture thread attached to a suture needle, the method comprising:
   grasping a first part of the suture thread by a first grasper inserted in the tubular organ, the suture thread having passed through a tissue surrounding the wound at a first position;
   moving the first part away from the first position by moving the first grasper grasping the first part along a longitudinal axis of the first grasper;
   grasping a second part of the suture thread by a second grasper inserted in the tubular organ, the second part being located between the first part and the first position; and
   moving the second part away from the first position by moving the second grasper grasping the second part along a longitudinal axis of the second grasper.

2. The method according to claim 1, wherein the longitudinal axis of the second grasper is parallel to the longitudinal axis of the first grasper.

3. The method according to claim 1, wherein the first grasper and the second grasper are both delivered to the wound through a channel of an endoscope.

4. The method according to claim 3, wherein the first grasper grasping the first part is moved along the longitudinal axis thereof relative to a distal end of the endoscope, and the second grasper grasping the second part is moved along the longitudinal axis thereof relative to the distal end of the endoscope.

5. The method according to claim 1, further comprising:
   releasing the first part of the suture thread grasped by the first grasper; and
   grasping a third part of the suture thread in between the second part and the first position by the first grasper.

6. The method according to claim 5, further comprising rotating an endoscope through which the first grasper and the second grasper extend to position the first grasper adjacent to the third part before grasping the third part.

7. The method according to claim 5, further comprising rotating an endoscope through which the first grasper and the second grasper extend while the third part is grasped by the first grasper so that the first grasper and the third part are moved in a direction away from the first position.

8. The method according to claim 7, further comprising:
   grasping a fourth part of the suture thread by the second grasper after rotating the endoscope, the fourth part of the suture thread being between the third part and the first position, and
   moving the fourth part of the suture thread away from the first position by moving the second grasper grasping the fourth part along the longitudinal axis of the second grasper.

9. The method according to claim 1, wherein the suture thread is passed through the tissue at the first position along a first direction that is transverse to the longitudinal axis of the first grasper and the longitudinal axis of the second grasper.

10. The method according to claim 1, wherein the suture thread is passed through the tissue at the first position along a first direction that is substantially orthogonal to the longitudinal axis of the first grasper and the longitudinal axis of the second grasper.

* * * * *